United States Patent [19]

Moore

[11] 4,038,973
[45] Aug. 2, 1977

[54] SYSTEM FOR MONITORING THE WEIGHT OF A PATIENT

[76] Inventor: Mary A. Moore, 5793 Truelson Drive, Fort Worth, Tex. 76134

[21] Appl. No.: 646,563

[22] Filed: Jan. 5, 1976

Related U.S. Application Data

[63] Continuation of Ser. No. 436,550, Jan. 25, 1974, abandoned.

[51] Int. Cl.$^2$ ............................................. A61G 11/00
[52] U.S. Cl. .................................................... 128/1 B
[58] Field of Search ............... 128/1 B, DIG. 29, 2 S, 128/2.06 R; 177/208, 209, 254, 242; 73/141; 340/279, 240

[56] References Cited

U.S. PATENT DOCUMENTS

| 2,598,532 | 5/1952 | Gibbon | 128/1 B |
| 3,217,818 | 11/1965 | Engelsher et al. | 177/144 |
| 3,372,764 | 3/1968 | Crotts | 177/208 |
| 3,433,316 | 3/1969 | Newman | 177/208 |
| 3,727,606 | 4/1973 | Sielaff | 128/2 S |
| 3,818,896 | 6/1974 | Deaton | 128/1 B |

Primary Examiner—Robert W. Michell
Assistant Examiner—Henry J. Recla
Attorney, Agent, or Firm—Richards, Harris & Medlock

[57] ABSTRACT

A system for monitoring the weight of a patient comprises a flexible but nonelastic envelope supported on a rigid support surface wherein said envelope has flexible upper and lower surfaces connected together in sealed relationship at spaced intervals forming a plurality of adjacent cells contiguous throughout the surface areas of said upper and lower surfaces. The envelope contains a fluid layer so that the pressure within the fluid layer is indicative of the total load supported on the receiving and supporting surface. A transducer responsive to the pressure of the fluid layer is provided for producing an electrical output indicative of the load supported on the receiving and supporting surface, and circuitry is coupled to the output of the transducer for selectively generating a visual readout indicative of the weight of a patient supported on the receiving and supporting surface and/or a change in the weight of the patient.

1 Claim, 9 Drawing Figures

SYSTEM FOR MONITORING THE WEIGHT OF A PATIENT

This is a continuation of application Ser. No. 436,550, filed Jan. 25, 1974, now abandoned.

BACKGROUND AND SUMMARY OF THE INVENTION

This invention relates to a system for monitoring the weight of a patient, and more particularly to a system for determining either the total weight or a change in the weight of a patient without disturbing the patient in any way.

In the treatment of small children and particularly infants, the quantity of medicine and other substances which are administered are now determined almost exclusively by the weight of the patient. It is therefore imperative to know the precise weight of the patient in order to assure the administration of the proper dosage of a medicine, etc. The determination of changes in the weight of the patient is also imperative not only in order to properly adjust the dosage of the medicine, etc. that is being administered, but also to determine the effect that the particular treatment is having on the patient.

Notwithstanding the necessity of knowing both the total weight and any change in the weight of an infant patient in order to facilitate proper treatment of the patient, there does not presently exist any satisfactory method for weighing critically ill babies. Thus, in accordance with current practices, it is necessary to remove an infant patient from the crib, incubator, etc. and to weigh the patient by means of a conventional baby scale of the type comprising a semicylindrical pan for receiving the patient and a pivoted beam having weights slidably supported thereon for use in determining the weight of the patient. While this procedure is satisfactory in the case of healthy babies, it will be understood that it can be very traumatic in the case of sick children, and can be totally unworkable in those instances in which catheters are in place or the infant is otherwise undergoing treatment.

There also exists a technique for weighing infants within an incubator enclosure. By means of this technique, the baby is positioned in a sling which is supported by a slender cable extending upwardly through the top of the incubator. The cable is connected to a scale supported on the top of the incubator which is utilized to weigh the baby. While this procedure eliminates the need of removing the infant from the incubator in order to determine his weight, it does not eliminate the necessity of disturbing the patient to a substantial extent in order to place him in and subsequently remove him from the weighing sling.

An accurate determination of at least changes in weight is also highly desirable during certain medical treatment procedures relating to adults. An example is that of kidney dialysis where changes in weight are utilized to determine the extent of treatment, and another example is in surgery where a determination of change of weight would be most helpful in determining the extent of blood loss, etc. In the case of kidney dialysis it is presently necessary to place the patient in a bed or chair which is situated on a scale mounted in the floor. While this technique is satisfactory for treatment facilities in which the scales are used relatively continuously, it is prohibitively expensive in those instances in which kidney dialysis treatment is performed infrequently. In the case of surgery, there does not presently exist a satisfactory system for determining changes in weight during the operating procedure.

The present invention relates to a system for monitoring the weight of a patient which overcomes the foregoing and other disadvantages long since associated with the prior art. In accordance with the broader aspects of the invention, there is provided a surface for receiving and supporting a patient with the entire weight of the patient supported by the surface. Structure is provided for producing an output indicative of the total load supported by the patient receiving and supporting surface. By this means the total weight of a patient and/or changes in the weight of a patient may be determined.

In accordance with more specific aspects of the invention, the patient receiving and supporting surface comprises a substantially horizontally disposed patient receiving and supporting surface. This surface is supported on a fluid layer so that the pressure within the fluid layer is indicative of the total load supported by the patient receiving and supporting surface. Transducer apparatus is provided which is responsive to the pressure of the fluid layer to produce an output indicative of the total load supported by the patient receiving and supporting surface, which in turn facilitates a determination of either the total weight of the patient or a change in the weight of a patient.

The patient receiving and supporting surface may comprise the upper surface of a flexible envelope having the fluid layer contained therein. In one embodiment of the invention such a device is positioned within an incubator to facilitate weighing of an infant patient housed therein without disturbing the patient in any way. In another embodiment of the invention a fluid-filled flexible envelope is incorporated in a portable infant weighing system adapted to facilitate both the determination of and the recording of the weight of healthy babies. In this embodiment a rigid patient receiving and supporting member is supported on the flexible envelope so as to eliminate any inaccuracy relating either to the physical size or movements of the patient. In still another embodiment of the invention the fluid-filled flexible envelope structure is utilized in conjunction with an otherwise conventional operating table to facilitate adult treatment procedures such as kidney dialysis, surgery, etc.

In a further embodiment of the invention a rigid patient receiving and supporting member is supported by a plurality of load cells. The output of the load cells is integrated to produce an output indicative of the total load supported by the rigid member and this output is in turn utilized to generate a visual readout indicative either of the total weight of a patient or of a change in the weight of a patient.

A still further embodiment of the invention is adapted to facilitate breathing of patients having severe fluid retention by supporting such patients in a head-elevated condition. In this embodiment the patient receiving and supporting structure may comprise either rigid members supported on load cells or a plurality of flexible but non-elastic envelopes.

DESCRIPTION OF THE DRAWINGS

A more complete understandng of the invention may be had by reference to the following Detailed Description when taken in conjunction with the accompanying Drawings, wherein.

DETAILED DESCRIPTION

Figure 1:
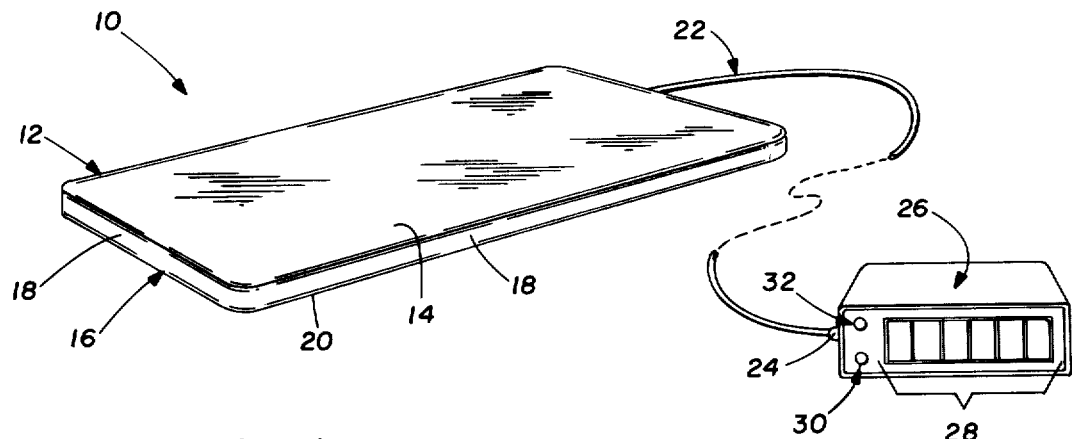
FIG. 1 is an illustration of the system for monitoring the weight of a patient incorporating the invention.

Referring now to the Drawings and particularly to FIG. 1 thereof, there is shown a system for monitoring the weight of a patient 10 incorporating the invention. The system 10 comprises an enclosure 12 having an upper surface 14 for receiving and supporting a patient with the body of the patient extending generally parallel to the surface and entirely supported thereby. The surface 14 may comprise the upper wall of a flexible but nonelastic envelope 16 further comprising side walls 18 and a bottom wall 20.

The enclosure 12 is filled with a fluid, which may comprise either a gas or a liquid. By way of example, the enclosure 12 can be filled with a gas such as compressed air or an inert gas such as helium, the major consideration being the absence of any flammable or poisonous gas within the enclosure 12. The enclosure 12 can also be filled with a liquid such as water or oil, again the major consideration being the absence of any dangerous substance within the enclosure. In the case of a liquid, the interior of the enclosure 12 is preferably provided with a series of baffles so as to prevent the formation of waves in the manner of a waterbed.

The system 10 further includes a hollow tubular passageway 22 connected in fluid communication with the interior of the enclosure 12 and extending to a transducer 24. The transducer 24 is responsive to the pressure within the enclosure 12 to produce an electrical output indicative of the total weight supported on the surface 14. The output of the transducer 24 is directed to electronic circuitry situated within a housing 26 which functions to convert the output of the transducer 24 to a visual readout 28. In the embodiment of the invention illustrated in FIG. 1, the visual readout 28 is digital, it being understood that other types of visual readouts may be utilized in the practice of the invention, if desired.

The electronic circuitry within the housng 26 is regulated by means of a conventional off/on switch 30 and an adjustment knob 32 which is utilized to cause the visual readout 28 to display the weight of the patient only. Thus, in the use of the system 10, items which will be supported on the surface 14 in addition to the patient, for example, sheets, blankets, and medical apparatus such as catheters, etc. are first positioned on the surface 14 and the knob 32 is adjusted to cause the visual readout 28 to read zero or nil. Thereafter, the patient is positioned on the surface 14 which causes the display 28 to exhibit the total weight of the patient.

As will be appreciated by those skilled in the art, in order for the system for monitoring the weight of a patient 10 to provide an accurate indication of the weight of a patient, the construction of the envelope 16 may be flexible, but should not be elastic. Moreover, since the transducer 24 and the circuitry within the housing 26 function to convert pressure into an indication of weight, the patient receiving and supporting surface 14 should be dimensioned for use in conjunction with a particular class of patients, i.e., infants, adults, etc. If it is desired to monitor the weight of patients which vary markedly in physical size by means of the system 10, the patient receiving and supporting surface 14 should be rigid so as to distribute the total weight of the patient over a uniform area.

Figure 5:
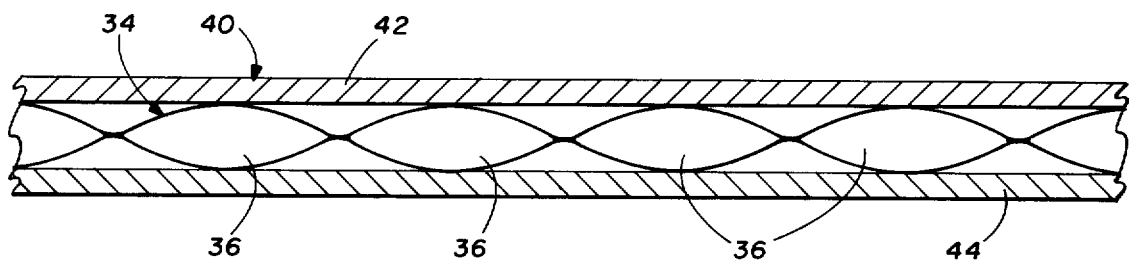
FIG. 5 is a sectional view illustrating a system for monitoring the weight of a patient incorporating the invention.
Figure 6:
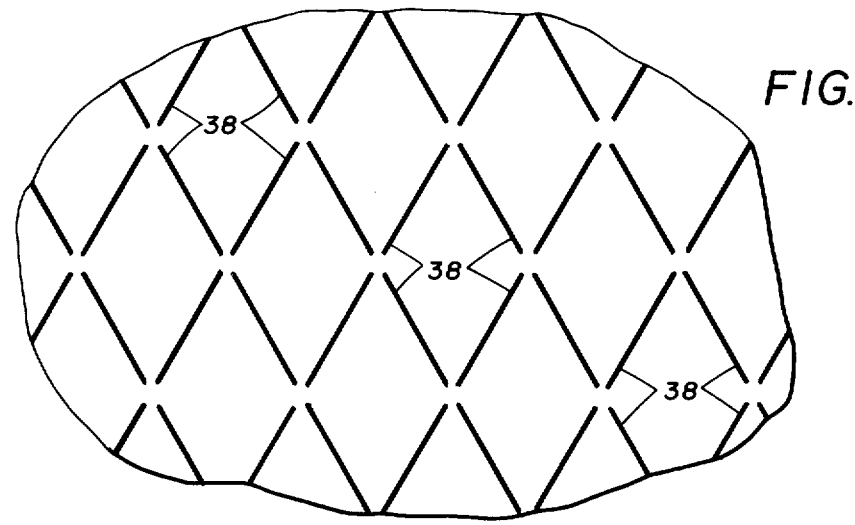
FIG. 6 is an illustration of the bonding pattern of the envelope of the system of FIG. 5.
Figure 7:
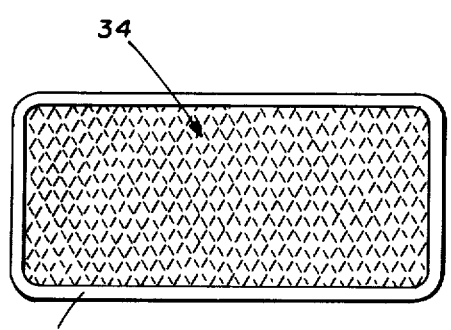
FIG. 7 is an illustration of a modified form of the system of FIG. 5.

An alternative construction which may be utilized in the system for monitoring the weight of a patient 10 is shown in FIGS. 5, 6 and 7. An envelope 34 formed from a flexible but nonelastic material is divided into a plurality of individual cells 36. As is shown in FIG. 6, the cells 36 may be formed by joining opposed sheets defining the envelope 34 along perpendicular lines 38, with open areas being maintained at the intersections of the lines 38 to permit fluid flow between adjacent cells. The use of the cells 36 in the envelope 34 is advantageous in that it prevents "bottoming" of any portion of the envelope 34 under the action of a concentrated load, such as the elbow, etc. of a patient.

The fluid which is utilized to fill the flexible envelope 34 may be either a liquid or a gas, the only criteria being that the fluid is incapable of causing injury should a leak develop in the flexible envelope 34. In the case of a liquid, the cells 36 further serve to prevent the formation of undesirable waves which might otherwise tend to travel the entire length of the envelope 34. Finally, the cells 36 substantially reduce fluctuations of the pressure within the envelope 34 which might otherwise occur due to movements of a patient.

The envelope 34 is preferably secured on one side to a rigid plate 40 having a patient receiving and supporting surface 42 and on the opposite side to a rigid plate 44. The plates 40 and 44 function to apply the total load supported on the surface 42 to the envelope 34 with minimum distortion of the envelope. By this means the system for monitoring the weight of a patient 10 utilizing the structure illustrated in FIGS. 5, 6 and 7 is adapted to accurately weigh a patient notwithstanding the physical size of the patient, and further notwithstanding the fact that the weight of the patient may be concentrated at particular points, i.e., the knees, the elbows, etc. In certain instances the plate 40 may be omitted in which case the patient is supported directly on the envelope 34. This is particularly true in the case of infants which tends to be relatively uniform in physical size and which do not tend to concentrate their weight at particular points. The plate 44 may also be deleted in certain instances, however, if both the plate 40 and the plate 44 are omitted, and particularly when the envelope 34 is filled with a gas, a rigid ring 46 of the type shown in FIG. 7 is preferably secured around the periphery of the envelope 34 to prevent the edges of the envelope from curling inwardly when a patient is received thereon.

Figure 2:
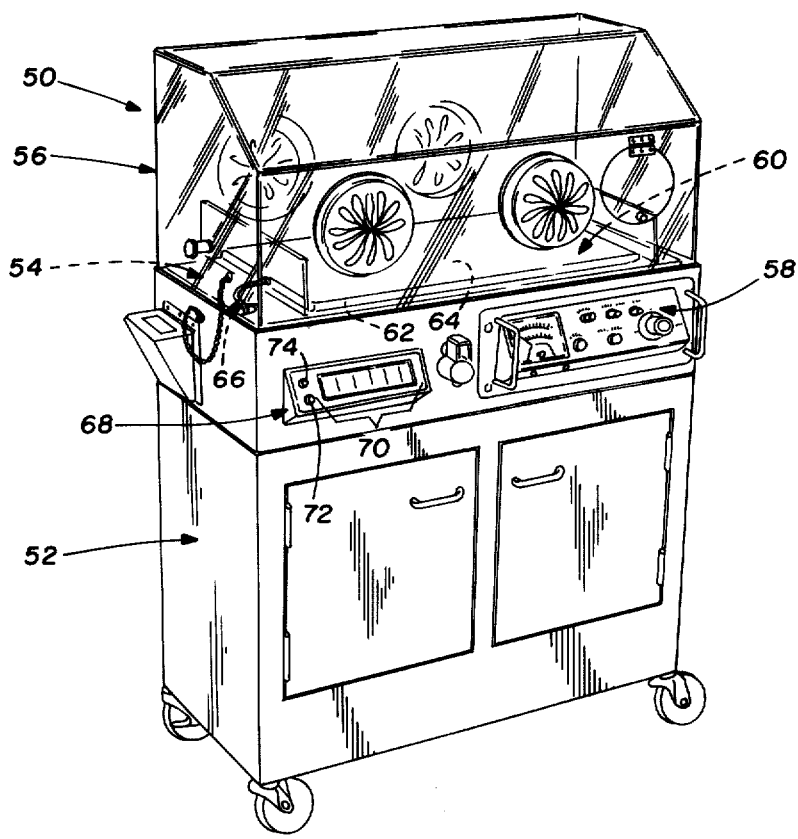
FIG. 2 is an illustration of an incubator utilizing the invention.

Referring now to FIG. 2, there is shown an incubator 50 utilizing the present invention. The incubator 50 includes a frame 52 having an upper support surface 54.

An enclosure 56 includes side walls extending upwardly from the periphery of the surface 54 and top walls extending over the surface 54. The incubator 50 includes various controls 58 which are utilized to regulate the environment within the enclosure 56. For example, the controls 58 regulate the temperature, the oxygen content, and other conditions within the enclosure 56, whereby the incubator 50 functions to substantially increase the changes of survival of an infant.

In accordance with the present invention, the incubator 50 is provided with a system 60 for monitoring the weight of an infant. The system 60 comprises a flexible envelope 62 mounted within the enclosure 56 and supported on the surface 54. The envelope 62 has an upper surface 64 for receiving and supporting an infant with the body of the infant extending generally parallel to the surface and entirely supported thereby. The envelope 62 is filled with a fluid which may comprise either a gas or a liquid, but which is non-flammable and otherwise incapable of causing injury to an infant should a leak develop in the envelope 62. In the case of a liquid, the interior of the envelope 62 is preferably provided with suitable baffles so as to prevent the formation of waves.

A hollow passageway 66 is connected in fluid communication with the interior of the envelope 62 and extends to a transducer (not shown). The transducer functions in response to the pressure within the envelope 62 to generate an electrical output indicative of the total weight supported by the surface 64. The output of the transducer is directed to circuitry situated within a housing 68 which functions to generate a visual readout 70 indicative of the weight of a patient supported on a surface 64. In the embodiment of the invention illustrated in FIG. 2 the visual readout is digital in nature, however, it will be understood that other conventional readouts may be utilized in the practice of the invention, if desired.

The system 60 further includes an off/on switch 72 and a control 74 which is utilized to eliminate the weight of objects which may be supported on the surface 64 other than an infant. In the use of the incubator 50, items such as sheets, blankets, catheters, etc. are first placed on the surface 64 and the control 74 is adjusted such that the visual readout 70 displays a reading of zero or nil. An infant is then positioned on the surface 64 and the enclosure 56 is closed. Thereafter, the system 60 is selectively utilized to determine the weight of the infant. In another use of the invention the control 74 is adjusted to cause the visual readout 70 to display zero or nil when the infant plus all sheets, blankets, catheters, etc. are first positioned on the surface 64. Thereafter, the system 60 may be utilized to determine changes of weight of the infant.

Those skilled in the art will appreciate the fact that the use of the weight monitoring system 60 in conjunction with the incubator 50 results in substantial advantages in infant care. At the present time the dosages of substantially all medicines, etc. which are administered to infants is determined by the weight of the infant patient. By means of the present invention it is possible to determine the infant's weight without disturbing the patient in any way, and without removing catheters, etc. which may be in use in the care of the patient. This in turn completely eliminates the trauma which so frequently accompanies the weighing of infant patients by means of prior art weighing systems.

It will be further understood that the embodiment of the invention illustrated in FIG. 2 is adapted for use in conjunction with incubators other than the type shown therein. For example, some types of incubators utilize an enclosure which does not include an upper wall, but instead utilizes side walls only to maintain a controlled atmosphere around an infant patient. The present invention is adapted for use with all types of incubator systems to determine the weight of an infant patient without removing the patient from the incubator or otherwise disturbing the patient.

Figure 3:
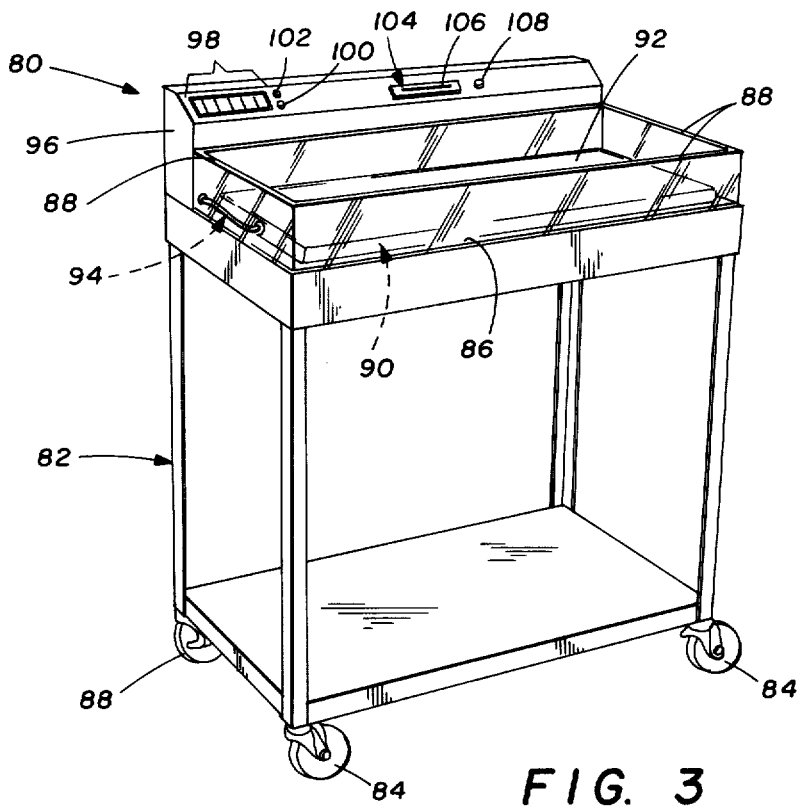
FIG. 3 is an illustration of an infant weighing apparatus utilizing the invention.

In FIG. 3 there is shown a mobile infant weighing apparatus 80 incorporating the invention. The apparatus 80 includes a frame 82 supported on wheels 84 and having a horizontally disposed upper support surface 86. The surface 86 is surrounded by side walls 88 which serve to prevent an infant from rolling off of the frame 82.

A flexible envelope 90 is supported on the surface 86 and is provided with a rigid upper surface 92 for receiving and supporting an infant with the body of the infant extending generally parallel to the surface and entirely supported thereby. The envelope 90 is filled with a fluid which may comprise either a gas or a liquid, but which is non-flammable and is otherwise wholly incapable of causing injury to an infant patient should a leak develop in the envelope 90. In the case of a liquid, the interior of the envelope 90 is provided with suitable baffles serving to prevent the occurrence of waves in the enclosed liquid.

The use of a flexible envelope 90 having a rigid upper surface 92 is particularly desirable in the mobile infant weighing apparatus 80. Thus, the apparatus 80 is intended for use in weighing patients which vary markedly in physical size, i.e., newborn infants through small children. The rigid upper surface 92 functions to distribute the weight of the patient uniformly over the entire envelope 90, and therefore provides an accurate reading regardless of the physical size of the patient.

A hollow tubular conduit 94 is connected in fluid communication with the interior of the envelope 90 and extends to a transducer (not shown). The transducer functions in response to the pressure within the envelope 90 to provide an electrical output indicative of the total weight supported on the surface 92. The output of the transducer is directed to electronic circuitry situated within the housing 96 which functions to provide a visual readout 98 indicative of the weight of an infant lying on the surface 92. The particular visual readout 98 illustrated in FIG. 3 is digital in nature, however, it will be understood that other conventional readouts may be utilized in the practice of the invention, if desired.

The mobile infant weighing apparatus 80 further includes an off/on switch 100 and a control 102 which is utilized to adjust the visual readout 98 to eliminate the weight of items supported on the surface 92 other than the infant being weighed. For example, the control 102 may be utilized to adjust the visual readout 98 so as to eliminate the weight of the sheets, blankets, etc. which are utilized in conjunction with the apparatus 80. The control 102 may also be used to eliminate the weight of diapers or other clothing which may be worn by an infant during the weighing procedure.

The mobile infant weighing apparatus 80 may also be provided with apparatus 104 for recording the weight of an infant. For example, the apparatus 104 may comprise a slot 106 adapted to receive a data processing card which is previously punched with the name or other information identifying the infant to be weighed, the date, etc. Such a card may be inserted into the slot 106 prior to the positioning of the infant on the surface 92. Then, when the infant is properly positioned on the surface 92, a switch 108 is actuated to cause the apparatus 104 to record the weight of the infant in the data processing card. The card then provides a permanent record of the weight of the infant which may be utilized by means of conventional data processing apparatus to monitor the progress of the infant and to diagnose any weight changes or trends which should be brought to the attention of the attending physician.

Figure 4:
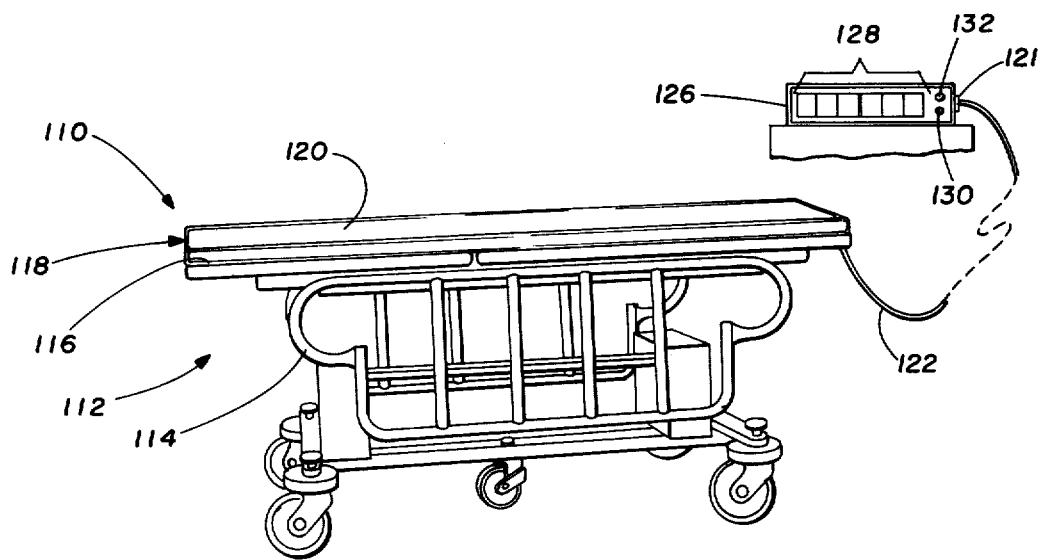
FIG. 4 is an illustration of an operating table utilizing the invention.

Referring to FIG. 4, the present invention is utilized in a system for monitoring the weight of a patient 110 which is particularly useful in conjunction with surgery, kidney dialysis, and similar procedures. An operating table 112 includes a frame 114 having an upper horizontally disposed support surface 116. A flexible envelope 118 is mounted on the surface 116 and includes an upper surface 120 for receiving and supporting a patient with the body of the patient extending generally parallel to the surface and entirely supported thereby. The envelope 118 includes a fluid which may be either a gas or a liquid, but which is nonflammable and is otherwise incapable of causing injury to a patient should a leak develop in the envelope 118. In the case of a liquid, the envelope 118 is provided with internal baffles serving to prevent the occurrence of waves in the confined liquid.

A hollow tubular conduit 122 is connected in fluid communication with the interior of the envelope 118 and extends to a transducer 124. The transducer 124 functions to convert the pressure within the envelope 118 to an electrical output indicative of the total weight supported on the surface 120. The output of the transducer 124 is directed to electronic circuitry situated within a housing 126 which functions to actuate a visual readout 128.

The system for monitoring the weight of the patient 110 further includes an off/on switch 130 and a control 132 which is used to regulate the operation of the visual readout 128. In the use of the system 110 a patient is positioned on the surface 120 together with all sheets, blankets, and medical apparatus which will be used in a particular procedure. The control 132 is then regulated to cause the visual readout 128 to display a zero or nil reading. Thereafter, the system 110 is utilized to display changes in weight of the patient by means of the visual readout 128.

As is well known, an indication of changes in weight is absolutely critical in such procedures as kidney dialysis. Such an indication is also highly useful in surgical procedures and the like. In suitable instances the visual readout 128 may be calibrated to display changes in weight in terms of the amount of blood lost during surgical procedures, etc.

Figure 8:
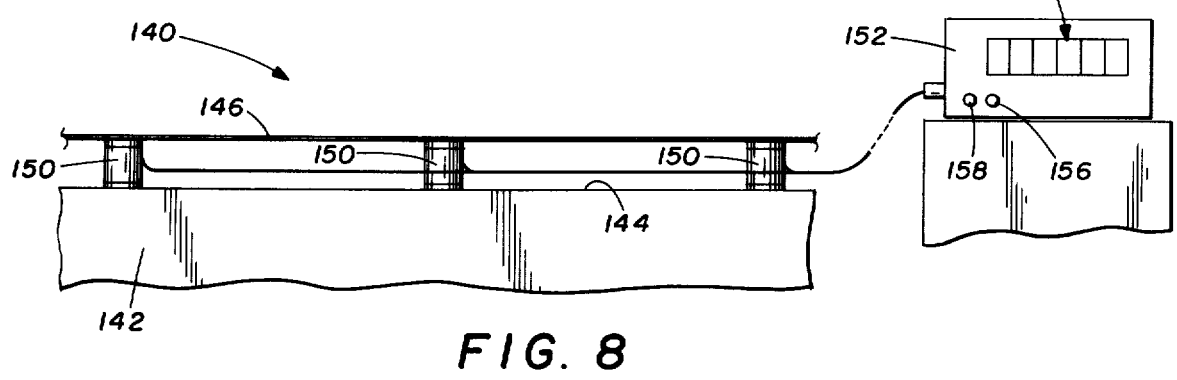
FIG. 8 is an illustration of an alternative system for monitoring the weight of a patient incorporating the invention.

In FIG. 8, there is shown an alternative system for monitoring the weight of a patient 140 incorporating the invention. The system 140 includes structure 142 having a rigid upper surface 144. A rigid patient receiving and supporting member 146 is supported over the surface 144 by a plurality of strain gauge type load cells 150.

The load cells 150 each produce an output indicative of the total load supported thereby. The outputs of the load cells 150 are directed to electronic circuitry located within a housing 152 which functions to integrate the outputs of the load cells 150 and thereby produce an output indicative of the total load supported on the patient receiving and supporting member 146. This output is in turn utilized to actuate a visual readout 154 which may be operated either to indicate the total weight of a patient or changes in the weight of a patient. The visual readout 154 illustrated in FIG. 8 is digital, however, it will be understood that other conventional types of readouts may be utilized in the practice of the invention.

The system 140 further includes an off/on switch 156 and a control switch 158. The switch 158 is utilized to adjust the visual readout 154 and thereby eliminates the weight of any extraneous objects which may be supported on the patient receiving and support member 146 in addition to the patient. The switch 158 may also be utilized to adjust the visual readout 154 to eliminate the initial weight of the patient, in which case the system 140 is utilized to indicate changes in the weight of the patient.

Figure 9:
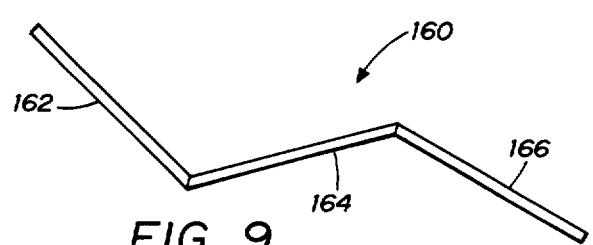
FIG. 9 is an illustration of an embodiment of the invention which may be utilized in the treatment of patients having severe fluid retention.

In FIG. 9 there is shown an embodiment of the invention useful in the treatment of patients having severe fluid retention. A patient receiving and supporting structure 160 is arranged to support a patient in a head-elevated condition, thereby facilitating breathing. The structure 160 comprises a series of interconnected members 162, 164 and 166 which support the back, thighs, and legs of the patient, respectively. The members 162–166 may comprise rigid members supported on load cells in the manner illustrated in FIG. 8. Alternatively, the members 162 may comprise fluid filled envelopes constructed as shown in FIGS. 5 and 6.

From the foregoing, it will be understood that the present invention comprises a system for monitoring the weight of a patient which incorporates numerous advantages over the prior art. Perhaps the most important of these advantages involves the fact that by means of the invention the weight of the patient may be determined without disturbing the patient in any way. Another important advantage involves the fact that by means of the invention either the total weight of the patient or changes in the weight of the patient may be determined with equal facility.

Although particular embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

What is claimed is:

1. A system for monitoring the weight of an infant patient comprising:
   incubator means for maintaining a predetermined atmosphere surrounding an infant patient and including enclosure means comprising a substantially rigid horizontal bottom wall and side walls extending upwardly from the bottom wall for cooperation therewith to define the enclosure means;
   an infant patient receiving and supporting flexible envelope supported on said bottom wall of the enclosure means of the incubator means and comprising a normally horizontally disposed, continuous flexible top wall for receiving and supporting an infant patient, with the entire weight of the patient being supported by said flexible top wall, and a flexible bottom wall underlying said flexible top wall and engaging said rigid bottom wall of the incubator means;

a fluid layer enclosed by the envelope and underlying and supporting the receiving and supporting flexible top wall of the envelope;

said fluid layer being enclosed by the envelope so that the pressure within the fluid layer is indicative of the total load supported on the receiving and supporting top wall thereof;

said flexible top and bottom walls of said flexible envelope being connected together in sealed relationship at spaced intervals forming a plurality of adjacent cells contiguous throughout the surface areas of said top and bottom walls, the sealing connections between said flexible walls being discontinuous so that said cells are interconnected for fluid communication to permit pressure equalization therebetween, said cells serving to prevent the formation of waves in the fluid layer enclosed by the flexible envelope;

transducer means responsive to the pressure within the envelope caused by the fluid layer for generating an electrical output indicative of the total load supported by the receiving and supporting top wall of the envelope with the receiving and supporting envelope in place on the bottom wall of the enclosure means of the incubator means and with the receiving and supporting top wall thereof in its normal horizontally disposed, substantially planar state; and means responsive to the electrical output of said transducer means for selectively generating a digital visual readout indicative of the total weight of an infant supported on the receiving and supporting top wall of the receiving and supporting envelope.

* * * * *